United States Patent
Carter et al.

(10) Patent No.: US 6,478,791 B1
(45) Date of Patent: Nov. 12, 2002

(54) TUCK AND FOLD FASCIA SHORTENING FOR INCONTINENCE

(75) Inventors: Garry L. Carter, Pleasanton, CA (US); David C. Densow, Livermore, CA (US); John P. Claude, San Carlos, CA (US); Paul L. Do, San Jose, CA (US); George A. Morrison, Foster City, CA (US)

(73) Assignee: SURX, Inc., Livermore, CA (US)

( * ) Notice: Subject to any disclaimer, the term of this patent is extended or adjusted under 35 U.S.C. 154(b) by 0 days.

(21) Appl. No.: 09/470,906

(22) Filed: Dec. 23, 1999

Related U.S. Application Data

(62) Division of application No. 09/103,352, filed on Jun. 23, 1998, now Pat. No. 6,044,847.

(51) Int. Cl.[7] .............................................. A61B 17/00
(52) U.S. Cl. .......................................... 606/1; 606/139
(58) Field of Search .......................... 606/1, 139, 151, 606/142, 143, 148, 152, 153, 45–50, 51, 52; 607/138

(56) References Cited

U.S. PATENT DOCUMENTS

| | | | |
|---|---|---|---|
| 3,575,158 A | 4/1971 | Summers | |
| 3,749,098 A | 7/1973 | DeBennetot | |
| 3,924,631 A | 12/1975 | Mancusi, Jr. | |
| 3,926,175 A | 12/1975 | Allen et al. | |
| 3,939,821 A | 2/1976 | Roth | |
| 4,016,881 A | * 4/1977 | Rioux et al. | 606/51 |
| 4,128,100 A | 12/1978 | Wenderoff | |
| 4,172,458 A | 10/1979 | Pereyra | |
| 4,418,692 A | * 12/1983 | Guay | 606/51 |
| 4,453,536 A | 6/1984 | Abild | |
| 4,633,861 A | 1/1987 | Chow et al. | |
| 4,686,962 A | 8/1987 | Haber | |
| 4,765,331 A | 8/1988 | Petruzzi et al. | |
| 4,773,393 A | 9/1988 | Haber et al. | |

(List continued on next page.)

FOREIGN PATENT DOCUMENTS

WO    WO 93/07815    4/1993

OTHER PUBLICATIONS

Raz, *Female Urology,* Second Edition, W.B. Saunders Company, Philadelphia, (1996) pp. 120, 340–342, 356–357.

Benson, *Female Pelvic Floor Disorders Investigation and Management,* Norton Medical Books, New York, (1992) pp. 239–240.

*Primary Examiner*—Michael Peffley
(74) *Attorney, Agent, or Firm*—Townsend and Townsend and Crew LLP

(57) ABSTRACT

Improved devices, methods, and systems for the surgical treatment of urinary incontinence generally enhance the support provided by the natural tissues of the pelvic floor without directly applying compressive pressure against the urethra. The invention provides probes for forming plications in the endopelvic fascia that are displaced laterally on either side of the midline. These probes can impose a predetermined level of trauma to the plicated tissues so as to promote the formation of adhesions. Adhesions can maintain the enhanced support provided by the plication after reabsorption of a temporary fastener (such as a reasborbable suture, staple, or the like). The plicating probe draws the tissue inward to provide a uniform plication within a predetermined size range.

15 Claims, 8 Drawing Sheets

U.S. PATENT DOCUMENTS

| | | | |
|---|---|---|---|
| 4,776,329 A | 10/1988 | Treharne | |
| 4,802,479 A | 2/1989 | Haber et al. | |
| 4,832,680 A | 5/1989 | Haber et al. | |
| 4,994,019 A | 2/1991 | Fernandez et al. | |
| 4,994,074 A | 2/1991 | Bezwada et al. | |
| 5,012,822 A | 5/1991 | Schwarz | |
| 5,035,696 A | 7/1991 | Rydell | |
| 5,133,727 A * | 7/1992 | Bales et al. | 606/170 |
| 5,140,999 A | 8/1992 | Ardito | |
| 5,149,329 A | 9/1992 | Richardson | |
| 5,156,315 A | 10/1992 | Green et al. | |
| 5,180,092 A | 1/1993 | Crainich | |
| 5,207,691 A | 5/1993 | Nardella | |
| 5,227,412 A | 7/1993 | Hyon et al. | |
| 5,234,409 A | 8/1993 | Goldberg et al. | |
| 5,256,133 A | 10/1993 | Spitz | |
| 5,304,123 A | 4/1994 | Atala et al. | |
| 5,314,465 A | 5/1994 | Maurer et al. | |
| 5,328,077 A | 7/1994 | Lou | |
| 5,376,064 A | 12/1994 | Cerny | |
| 5,395,034 A | 3/1995 | Allen et al. | |
| 5,403,312 A * | 4/1995 | Yates et al. | 606/50 |
| 5,403,326 A * | 4/1995 | Harrison et al. | 606/139 |
| 5,411,475 A | 5/1995 | Atala et al. | |
| 5,437,603 A | 8/1995 | Cerney et al. | |
| 5,439,479 A * | 8/1995 | Shichman et al. | 606/220 |
| 5,458,596 A | 10/1995 | Lax et al. | |
| 5,470,009 A | 11/1995 | Rodak | |
| 5,576,418 A | 11/1996 | Jurgens | |
| 5,611,515 A | 3/1997 | Benderev et al. | |
| 5,662,259 A | 9/1997 | Yoon | |
| 5,735,445 A | 4/1998 | Vidal et al. | |
| 5,947,983 A * | 9/1999 | Solar et al. | 606/144 |
| 6,091,995 A * | 7/2000 | Ingle et al. | 607/138 |

* cited by examiner

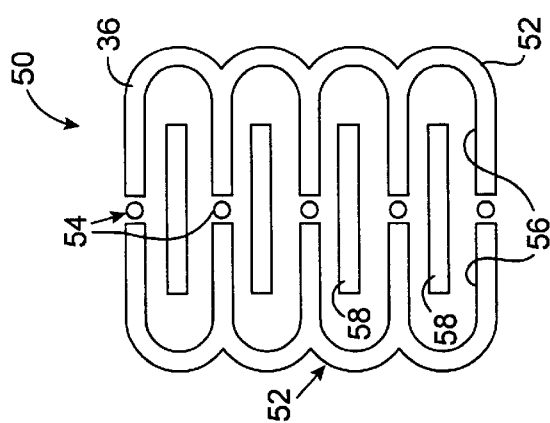
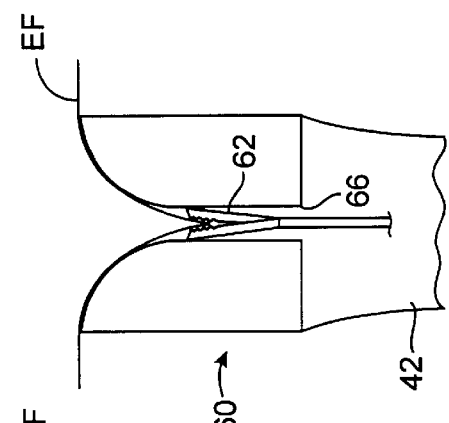
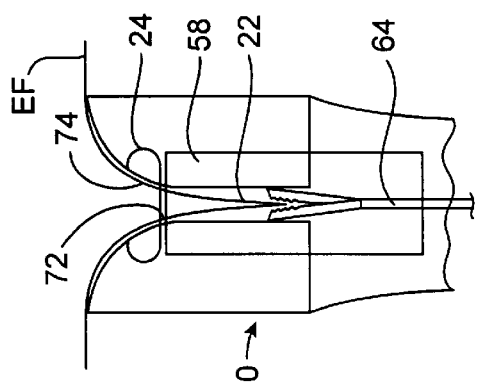
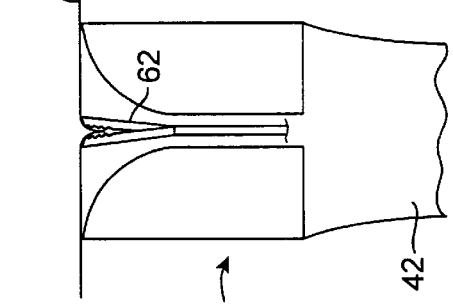
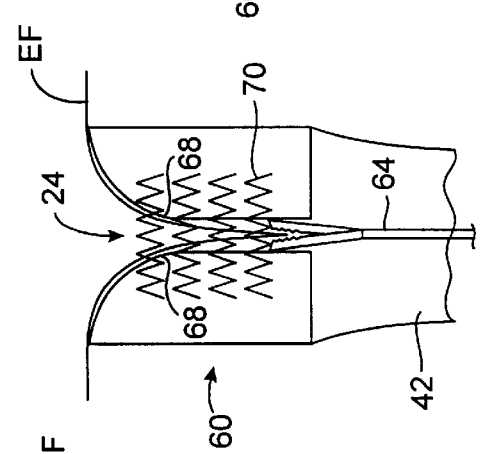
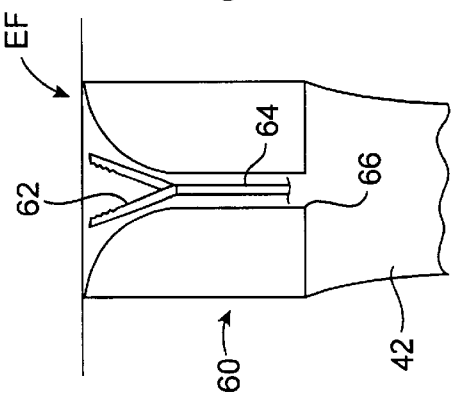
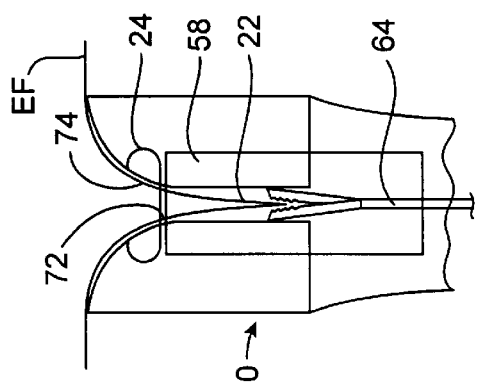

TUCK AND FOLD FASCIA SHORTENING FOR INCONTINENCE

CROSS-REFERENCES TO RELATED APPLICATIONS

The present application is a divisional patent application of and claims the benefit of priority from U.S. patent application Ser. No. 09/103,352 filed Jun. 23, 1998, now U.S. Pat. No. 6,044,847, the full disclosure of which is incorporated herein by reference.

BACKGROUND OF THE INVENTION

1. Field of the Invention

The present invention generally relates to medical devices, methods and systems, particularly for the treatment of urinary incontinence.

Urinary incontinence arises in both men and women with varying degrees of severity, and from different causes. In men, the condition frequently occurs as a result of prostatectomies which result in mechanical damage to the sphincter. In women, the condition typically arises after pregnancy when musculoskeletal damage has occurred as a result of inelastic stretching of the structures which support the genitourinary tract. Specifically, pregnancy can result in inelastic stretching of the pelvic floor, the external sphincter, and the tissue structures which support the bladder and bladder neck region. In each of these cases, urinary leakage typically occurs when a patient's abdominal pressure increases as a result of stress, e.g., coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt a behavior modification intended to reduce the incidence of urinary leakage.

In cases where such non-interventional approaches are inadequate or unacceptable, the patient may undergo surgery to correct the problem. A wide variety of procedures have been developed to correct urinary incontinence in women. Several of these procedures are specifically intended to support the bladder neck region. For example, sutures, straps or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

An alternative procedure which is often performed to enhance support of the bladder is the Kelly plication. This technique involves midline plication of the fascia, particularly for repair of central defects. In this transvaginal procedure, the endopelvic fascia from either side of the urethra is approximated and attached together using silk or linen suture. A similar procedure, anterior colporrhaphy, involves exposing the pubocervical fascia and reapproximating or plicating portions of this tissue from either side of the midline with absorbable sutures. While the Kelly plication and its variations are now often used for repair of cystocele, this procedure was originally described for the treatment of incontinence.

Each of these known procedures has associated shortcomings. Surgical operations which involve midline plications or direct suturing of the tissue structures supporting the urethra or bladder neck region require great skill and care to achieve the proper level of artificial support. In other words, it is necessary to occlude or support the tissue sufficiently to inhibit urinary leakage, but not so much that intentional voiding is made difficult or impossible. Balloons and other bulking agents which have been inserted can migrate or be absorbed by the body. The presence of such inserts can also be a source of urinary tract infections.

For these reasons, it would be desirable to provide improved devices, systems and methods for treating urinary incontinence in men and women. In particular, it would be desirable to provide techniques for treating urinary incontinence which did not artificially compress or obstruct the urethra, but which enhanced the support and functioning of the patient's natural pelvic tissue structures. It would further be desirable if these improved techniques could be performed rapidly in a minimally invasive manner and with good efficacy, despite normal variations in individual surgeon's surgical skills and experience.

2. Description of the Background Art

The impact of surgical treatments of the urethra were described in *Female Urology*, 2nd Ed., by Shlomo Raz (1996). This reference also describes techniques of surgical repair for treatment of cystocele (including the Kelly plication and the Burch procedure) on pages 340–342, while various alternative known surgical interventions for treatment of incontinence are schematically illustrated on page 356. At least some of these procedures are also described in *Female Pelvic Disorders, Investigation And Management* by J. Thomas Benson (1992) on pages 239–240.

The following patents and published applications relate to the treatment of urinary incontinence. U.S. Pat. Nos. 5,437,603; 5,411,475; 5,376,064; 5,314,465; 5,304,123; 5,256,133; 5,234,409; 5,140,999; 5,012,822; 4,994,019; 4,832,680; 4,802,479; 4,773,393; 4,686,962; 4,453,536; 3,939,821; 3,926,175; 3,924,631; 3,575,158; 3,749,098; and WO 93/07815.

An electrosurgical probe for the controlled contraction of tissue of joints and for dermatological indicators is described in U.S. Pat. No. 5,458,596. A bipolar electrosurgical probe having electrodes formed over a restricted arc of its distal end for treatment of, e.g., the esophagus, as described in U.S. Pat. No. 4,765,331. An electrosurgical probe for retrograde sphincterotomy is described in U.S. Pat. No. 5,035,696.

SUMMARY OF THE INVENTION

The present invention provides improved devices, methods, and systems for the surgical treatment of urinary incontinence. The techniques of the present invention generally enhance the support provided by the natural tissues of the pelvic floor without directly applying compressive pressure against the urethra. The invention provides methods and probes that are particularly well suited for forming plications in the endopelvic fascia which are displaced laterally on either side of the midline. In the preferred embodiments, the plication probes impose a predetermined level of trauma to the approximated tissues so as to promote the formation of adhesions. These tough fibrous scar tissues can maintain the enhanced support provided by the reduction in effective support tissue length after reabsorption of a temporary fastener (such as a reabsorbable suture, staple, or the like). The use of a plicating probe which draws the tissue laterally inward toward the probe and affixes the plication not only speeds up the procedure, but also provides a fold having a fold depth within a predetermined size range so as to effectively inhibit incontinence.

In a first aspect, the present invention provides a therapy for incontinence. The therapy comprises engaging an endopelvic support tissue with a probe, and manipulating the engaged tissue with the probe to form a fold having a first portion of the tissue adjacent to a second portion of the tissue along a fold depth, the fold depth being within a predetermined range. The first and second tissue portions are then affixed together with the probe to decrease a dimension of the tissue such that incontinence is inhibited.

Generally, the tissue portions will comprise the endopelvic fascia. This tissue will ideally be drawn laterally inward to fold either towards or away from the probe, the tissue often being affixed into two separate folds disposed on opposite sides of (and separated from) the urethra. The approximated portions of the endopelvic fascia may be affixed together by advancing a fastener from the probe at least partially through each tissue portion. Suitable fasteners include suture, staples, barbed tacks, helical coils, and the like, and will preferably be at least partially bio-absorbable. Where bio-absorbable fasteners are used, the probe will preferably also promote adhesion formation between the first and second tissue portions by abrading the adjacent tissue surfaces, by transmitting an electrical current through the tissues, or the like. The probe will often draw the tissue portions towards each other so as to define a tissue fold having a tissue depth of between about 2.0 mm and 2.0 cm from the tissue surface.

In another aspect, the present invention provides a therapy for incontinence of a patient. The patient has endopelvic fascia extending laterally on first and second sides of the urethra. The therapy comprises affixing a first surface region of the endopelvic fascia on the first side of the urethra to a second surface region of the endopelvic fascia which is also on the first side of the urethra. These regions are affixed with a first fastener to as to decrease an effective length of the first side. The shortened effective lengths of the endopelvic fascia enhances the support of the urethra such that incontinence is inhibited.

Optionally, an asymmetric modification of the endopelvic fascia may effectively inhibit incontinence without treating the second side. The urethra may be laterally deflected, or the treatment may simply compensate for an asymmetric stretching of the tissue. More commonly, a third surface region of the endopelvic fascia on the second side of the urethra is affixed to a fourth surface region of the endopelvic fascia on the second side of the urethra with a second fastener so as to decrease an effective length of the second side.

In another aspect, the present invention provides an endopelvic fascia plication tool. The tool comprises a probe having a proximal end and a distal end. Means are disposed near the distal end for grasping a region of the endopelvic fascia. An actuation mechanism is coupled to the grasping means. Actuation of this mechanism draws the grasped region inward from an initial configuration having an initial area to a smaller configuration having a smaller area.

As used herein, the phrases "drawing the tissue inward" (and the like) encompasses the formation of tissue folds extending towards and/or away from the probe. The plication tool will also often include means for affixing the inward drawn region in the small configuration. The affixing means will typically comprise an electrode, adhesive, suture, staple, helical coil, barbed tack, or the like. In many of these embodiments, the affixing means will be reabsorbable, and the plication tool will further comprise means for promoting adhesion formation during the healing process. This adhesion promoting means will generally be oriented for engaging a surface of the endopelvic fascia disposed within a fold of the endopelvic fascia, the fold being formed as the grasped region is drawn inward from the initial configuration to the smaller configuration.

In yet another aspect, the present invention provides an endopelvic fascia plication system. The system comprises a probe having a proximal end and a distal end. A grasper is disposed adjacent the distal end for engaging a surface region of the endopelvic fascia. A first actuation mechanism is coupled to the grasper so that actuation of the first mechanism draws the engaged tissue inward from an initial configuration to a smaller areal configuration.

In yet another aspect, the present invention provides a therapy for incontinence. The therapy comprises decreasing a first effective length of an endopelvic fascia between a urethra and a first arcus tendinous fascia pelvis. A second effective length of the endopelvic fascia between the urethra and a second arcus tendinous fascia pelvis is also decreased. The first and second lengths are separated from the urethra so as to avoid directly compressing the urethra, thereby inhibiting incontinence without obstructing voluntary voiding.

In yet another aspect, the invention provides an incontinence therapy kit. The kit comprises a probe having a tissue folding mechanism. Instructions for using the probe are also provided. The instructions describe a method which includes the steps of forming a laterally offset fold in the endopelvic fascia and affixing the fold so as to inhibit incontinence.

BRIEF DESCRIPTION OF THE DRAWINGS

FIGS. 9A–9C illustrate a plication tool having hinged graspers which pull the fascia inward while roughened retainer structures force the fascia to fold in the desired direction, the roughened retainer structures abrading the fascia to promote adhesions upon resorption of staples.

FIGS. 10A–10F schematically illustrate a plication tool and method in which forceps draw a region of the endopelvic fascia proximally into a fixed channel defined by slide surfaces, and in which the endopelvic fascia is affixed in the folded configuration at least in part by transmitting a bipolar current between the slide surfaces of the tool.

DESCRIPTION OF THE SPECIFIC EMBODIMENTS

The present invention generally provides methods, devices, and systems which inhibit incontinence by selectively reducing an effective length of the endopelvic fascia or other endopelvic support tissues. The methods and devices of the present invention will often be used to form folds in the endopelvic fascia which extend substantially in an anterior-posterior orientation, and which are displaced laterally from the urethra. The probes of the present invention will be adapted to engage and form plications having a fold length within a predetermined range suitable for effecting the desired therapy, thereby minimizing the variability in results which normally occur with variations in surgeons skill, experience, and the like. These probes will also often include a mechanism to affix the approximated tissues together, often using fasteners, electrosurgical potential, adhesive, or the like. Where the probe further includes a mechanism for promoting the formation of adhesions, the affixing mechanisms need only temporarily affix the fold as the tough, fibrous, adhesions can maintain the enhanced support of the shortened fascial tissue upon completion of the healing process. These techniques will find applications in a wide variety of therapies, including for inguinal hernias, abdominal hernias, ligament shortening, shoulder capsule reduction, correction of paravaginal defects, and stomach reduction. The most immediate application for the invention, however, will be to enhance the patient's own natural support of the bladder, bladder neck region, and urethra so as to inhibit urinary incontinence.

Figure 1:
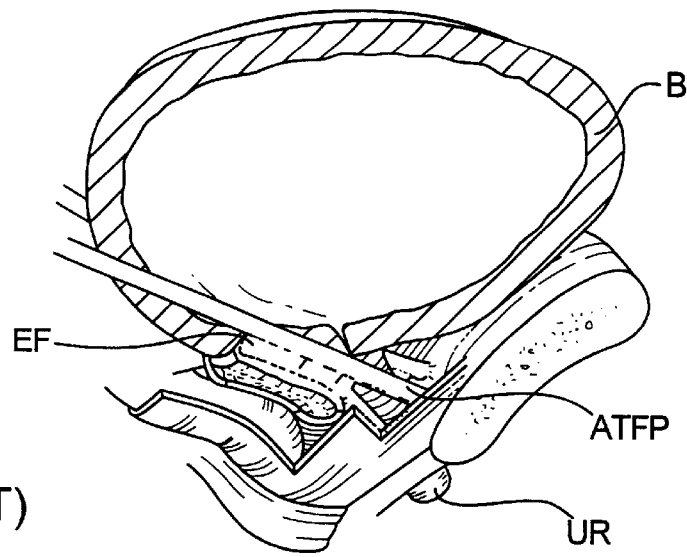
FIG. 1 is a lateral cross-sectional view showing the urinary bladder and bladder support structures.

The pelvic support tissues which generally maintain the position of much of the genital urinary tract, and particularly the position of urinary bladder B, are illustrated in FIG. 1. Of particular importance for the method of the present invention, endopelvic fascia EF defines a hammock-like structure which extends between the left and right arcus tendinous fascia pelvis ATFP. These latter structures extend substantially between the anterior and posterior portions of the pelvis, so that the endopelvic fascia EF largely defines the pelvic floor.

In women with urinary stress incontinence due to bladder neck hypermobility, the bladder has typically dropped between about 1.0 cm and 1.5 cm (or more) below its nominal position. This condition is typically due to weakening and/or stretching of the pelvic support tissues, including the endopelvic fascia, the arcus tendinous fascia pelvis, and the surrounding ligaments and muscles, often as a result of bearing children.

When a woman with urinary stress incontinence sneezes, coughs, laughs, or exercises, the abdominal pressure often increases momentarily. Such pressures pulses force the bladder to descend still farther, shortening the urethra UR and momentarily opening the urinary sphincter.

Figure 2:
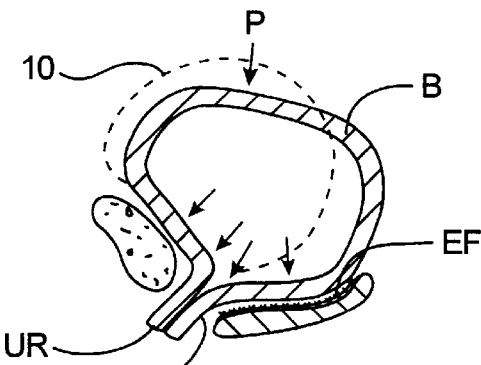
FIG. 2 is a cross-sectional view of a patient suffering from urinary stress incontinence due to inelastic stretching of the endopelvic fascia.
Figure 3:
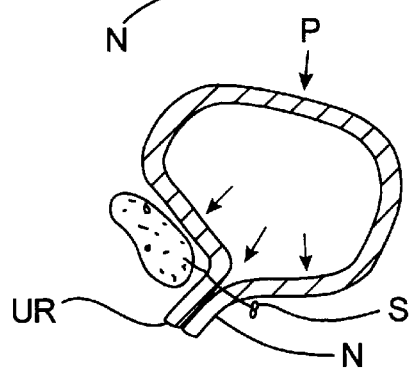
FIG. 3 shows a known method for treating urinary incontinence by affixing sutures around the bladder neck.
Figure 4:
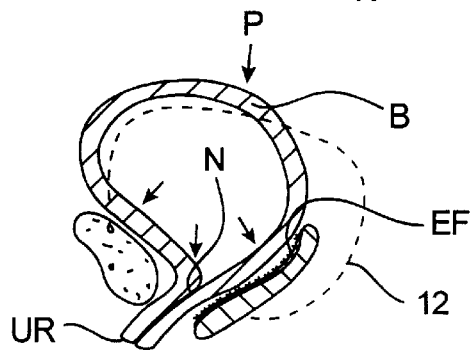
FIG. 4 illustrates improved bladder support provided by decreasing an effective length of the endopelvic fascia according to the principles of the present invention.

As can be most clearly understood with reference to FIGS. 2–4, the present invention generally provides a therapy which effectively reduces the length of the pelvic support tissues and returns bladder B towards its nominal position. Advantageously, the bladder is still supported by the fascia, muscles, ligaments, and tendons of the natural pelvic support tissues.

Referring now to FIG. 2, bladder B can be seen to have dropped from its nominal position (shown in phantom by outline 10). While endopelvic fascia EF still supports bladder B to maintain continence when the patient is at rest, a momentary pulse P opens the bladder neck N resulting in a release through urethra UR.

A first known treatment for urinary stress incontinence relies on suture S to hold bladder neck N closed so as to prevent inadvertent voiding, as seen in FIG. 3. Suture S may be attached to bone anchors affixed to the pubic bone, ligaments higher in the pelvic region, or the like. In any case, loose sutures provide insufficient support of bladder neck N and fail to overcome urinary stress incontinence. Over tightening suture S may make normal urination difficult and/or impossible.

As shown in FIG. 4, by reducing the effective length of the natural pelvic support tissues, bladder B can be elevated from its lowered position (shown by lowered outline 12). A pressure pulse P will then be resisted in part by endopelvic fascia EF which supports the lower portion of the bladder, helping maintain the bladder neck in a closed configuration. In fact, fine tuning of the support provided by the endopelvic fascia is possible through selective plication of the anterior portion of the endopelvic fascia. To close the bladder neck and raise bladder B upward, for example, it may be possible to increase a length of a fold towards the front. Alternatively, repositioning of bladder B to a more forward position may be affected by selectively plicating the dorsal portion of the endopelvic fascia EF to a greater extent than the forward portion. Hence, the therapy of the present invention may be tailored to the particular weakening exhibited by a patient's pelvic support structures. Regardless, the portion of the endopelvic fascia EF adjacent the bladder neck and urethra UR can remain free of sutures or other artificial support structures which might directly compress the urethra.

Figure 5:
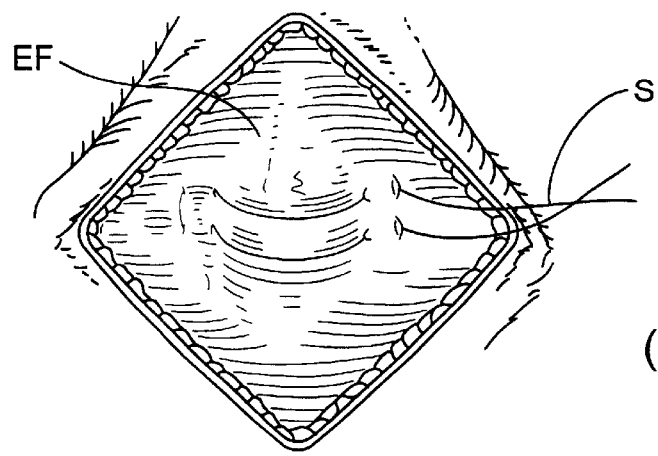
FIGS. 5 and 6 illustrate the Kelly plication, a known method for supporting the bladder for patients having tears or other central defects, but which may directly compress the urethra and make voluntary voiding difficult.
Figure 6:
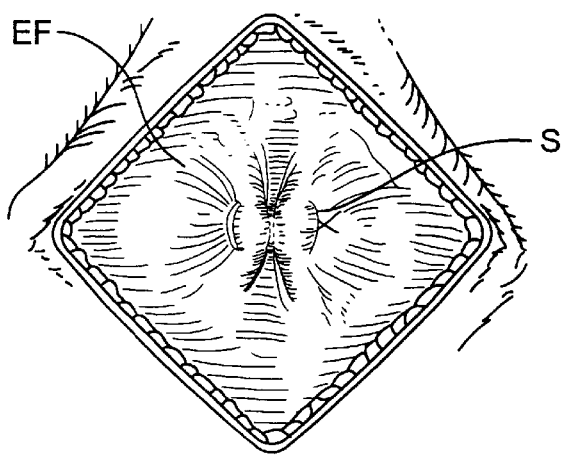

An alternative known procedure for enhancing the support of the bladder, particularly as a therapy for cystocele, is the Kelly plication, as illustrated in FIGS. 5 and 6. These techniques involve midline plication of the endopelvic fascia. In the original Kelly plication, the midline of the vaginal wall is incised and the endopelvic fascia is then dissected for between about 2 cm to 2.5 cm at the level of the bladder neck. Lateral portions of the endopelvic fascia from either side of the urethra are approximated with silk or linen suture. Optionally, a relatively large (such as a 16 Fr) catheter may be placed within the urethra prior to positioning and tying of the sutures in an effort to prevent subsequent stenosis. Nonetheless, as can be seen with reference to FIG. 6, the sutures extend across the midline and thereby potentially directly compress the urethra once the procedure is complete.

Figure 7:
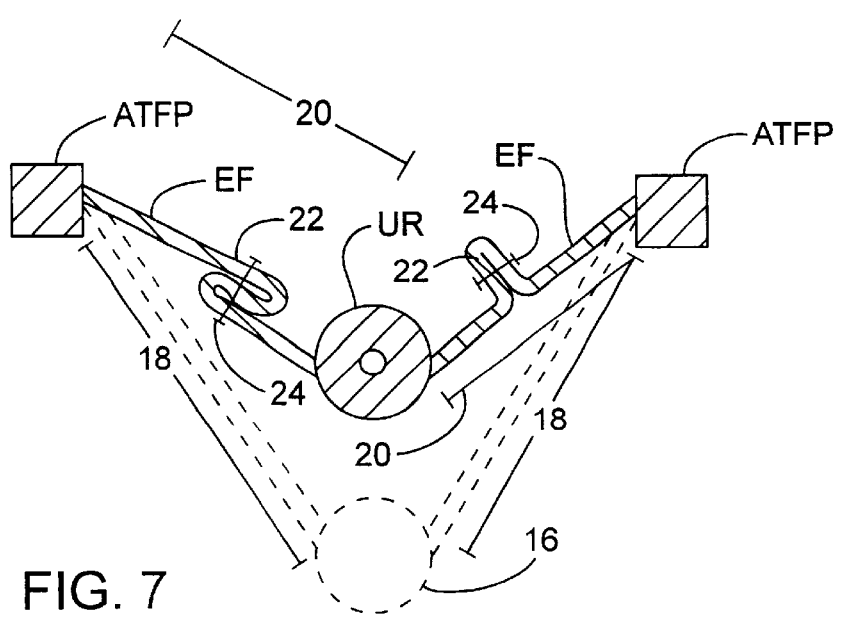
FIG. 7 schematically illustrates the laterally displaced plications of the present invention which decrease effective lengths of the endopelvic fascia on both sides of the urethra so as to enhance support without compressing or obstructing the urethra.
Figure 8A:
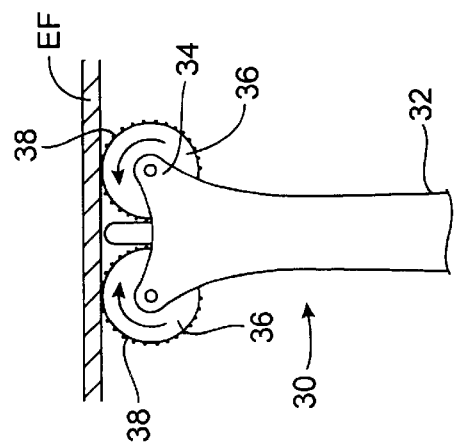
FIGS. 8A–8F illustrate a plication probe and method for its use in which rollers having a roughened surface or protrusions abrade the tissue surface and draw the endopelvic fascia inward while a smooth retainer structure extends to control the direction of the fascial fold.
Figure 8B:
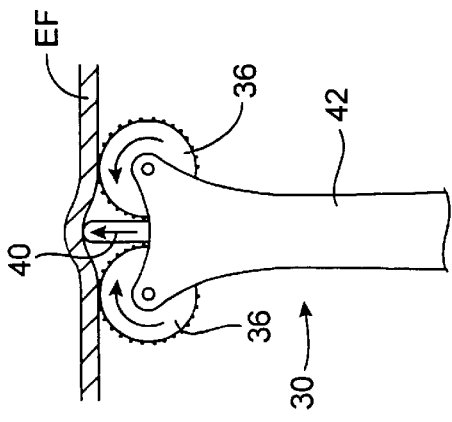
Figure 8C:
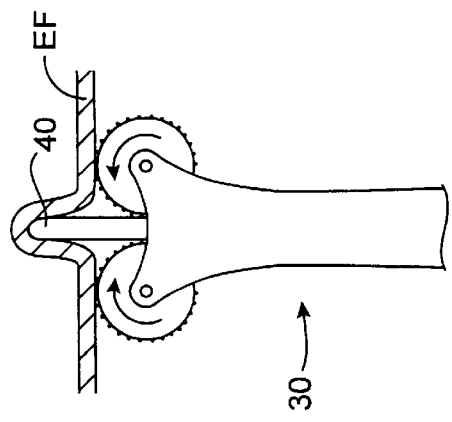
Figure 8D:
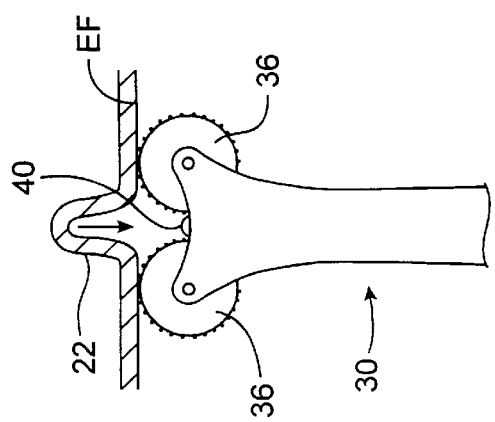
Figure 8E:
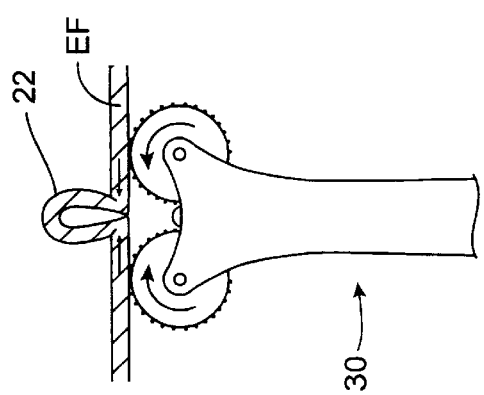
Figure 8F:
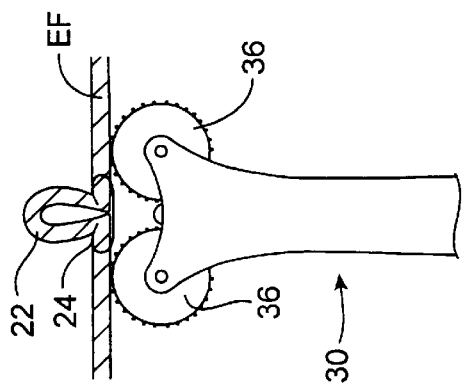

Referring now to FIG. 7, the anatomy of the urethral support structures is schematically illustrated. Researchers have attributed continence during transitory pulses such as coughing to a variety of mechanisms. Several researchers have attributed continence during coughing to rapid contraction in the muscles supporting the pelvic floor. However, other studies have shown that there is no pelvic floor contraction during stress, and that continence is instead maintained by the position of the proximal urethra. Since the increasing urethral pressure is not caused by muscles tightening the endopelvic fascia, others have speculated that continence is maintained by effective abdominal pressure transmission. Although much data has been published concerning pressures in the urethra and bladder for incontinent and continent women, patient to patient variations in pressure have been so large that no generalized correlations between pressure and continence have been established.

It is possible that timing of pressure pulses, rather than the total pressure or muscular contraction of the pelvic floor, may be one of the critical factors for determining continence. When a continent woman coughs, the pressure in the urethra increases more than 1/10 of a second prior to the increase in bladder pressure. In women with stress incontinence, the bladder pressure rises first, leading to leakage until the transmitted pressure is able to close the urethra (1/10 to 1/2 second later).

Using this analysis, a woman having a stretched endopelvic fascia (as shown by outline 16) would tend to have a greater time delay between the initiation of pressure in the bladder and the transmission of sealing pressure against the urethra UR. Basically, it takes time for the lengthened fascia to stretch to the point that the tension imposed by the endopelvic fascia on the urethra is sufficient to seal the urethra.

To decrease the time delay between the initiation of a pressure pulse and an imposition of a sealing force against the urethra, the methods of the present invention generally decrease the effective length of the endopelvic fascia on either side of the urethra from an initial length 18 to a shortened length 20. These lengths are generally decreased by forming folds 22 in the endopelvic fascia EF. These folds will often at least initially be supported using fasteners 24.

Fasteners 24 may comprise any of a variety of temporary or permanent structures. Suitable fasteners include sutures, staples, barbed tacks, helical coils, adhesives, or the like. These fasteners may be formed of any biocompatible material, and can optionally permanently affix the fold. Alternatively, imposing a controlled damage or trauma to the interior surfaces of the folds will promote the formation of adhesions. As the adhesions may be used to permanently affix the fold and maintain the shortened length of the endopelvic fascia EF, fasteners 24 may instead be formed of a reabsorbable material.

The folds will typically extend along a fold depth from about 2.0 mm to about 2.0 cm, and will often be aligned along an anterior-posterior direction for a length greater than their depth, the fold length typically being from about 1.0 cm to about 3.0 cm. Such elongated folds may be held with a plurality of separate fasteners, the number and spacing of the fasteners often being determined by their ability to contiguously approximate the fold so that the sides, over time, are connected by scar tissue. The folds may extend away from the major surfaces of the endopelvic fascia towards or away from the plication tool, and may optionally lay flattened against these surfaces, as shown in FIG. 7. Regardless, this effective shortening of the endopelvic fascia, together with any stiffening of the fascial structure (through the formation of adhesions, the application of heat or radiofrequency potential, or the like) will be sufficient to improve the support of the urethra, bladder neck, and bladder so that incontinence is inhibited.

A variety of probe structures could be used to perform the above method. Referring now to FIGS. 8A–8F, a roller probe 30 generally has a proximal portion 32 and the distal end 34. Rollers 36 have roughened surfaces 38. These roughened surfaces may initially be drawn across the fascia so as to abrade it. Distal end 34 then firmly engages a surface of endopelvic fascia EF, and cylinders 36 are rotated so the distal portion of surfaces 38 move inward towards each other. Roughened surfaces 38 grab the fascia and draw it inward.

As cylinders 36 rotate, a smooth fold retainer structure 40 gradually extends distally from a shaft 42 of probe 30 to form fold 42 in the desired direction. Retainer 40 may be used to measure the length of the fold, and can recoil proximally to allow the cylinders to draw the fold into contact with itself (see FIGS. 8D and 8E).

Once fold 22 is formed, fastener 24 (here in the form of a staple) is deployed from probe 30 to affix the fold in position until adhesions have formed. One or more staples 24 may be deployed using conventional tissue stapler structures, the tissue staplers often being disposed between pairs of rollers 36 so as to intermittently support an elongate fold 22 along the length of the fold. Alternatively, the fold may be affixed in position using a separate probe structure. Similarly, the inner surfaces of the fold may be abraded or otherwise traumatized so as to promote the formation of adhesions using a separate structure. Suitable stapler structures and stapling methods are described in U.S. Pat. Nos. 5,735,445; 5,470,009; 5,180,092; 5,156,315; 4,633,861; 5,662,259; 5,395,034; and 4,465,896, the full disclosures of which are incorporated herein by reference.

Figure 9B:
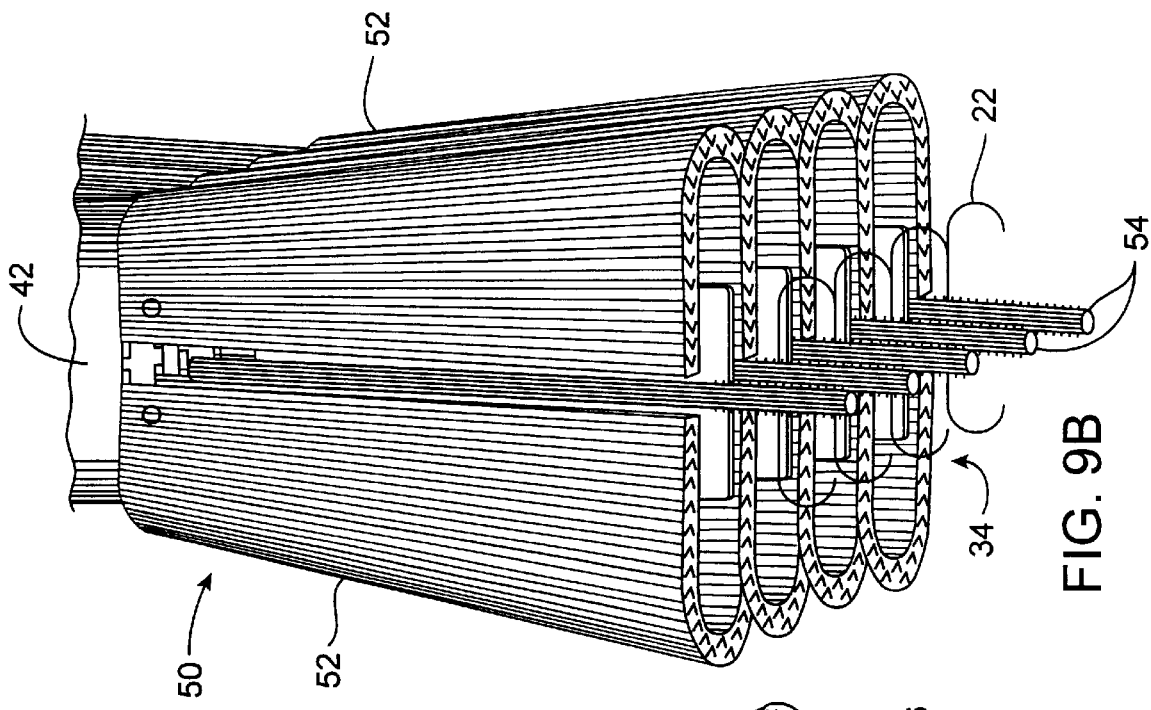
Figure 9A:
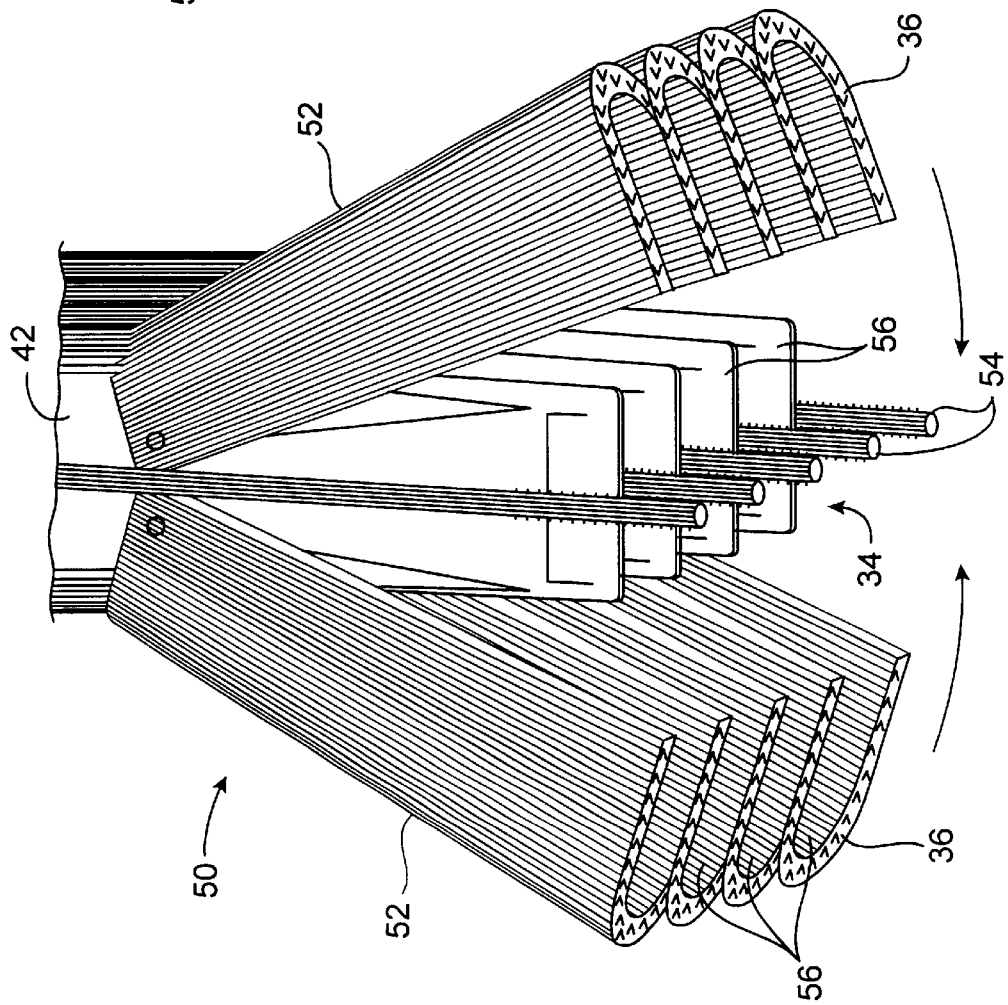

Referring now to FIGS. 9A–9C, a pivotal plication probe 50 includes a pair of arms 52 that pivot relative to shaft 42. Arms 52 again have roughened surfaces 36 to engage and draw the fascial surface inward. As the grasping arms close towards each other, roughened fold retainers 54 move distally relative to shaft 42, thereby urging the tissue surface to form fold 22 in the desired direction.

Arms 52 define a plurality of inwardly oriented channels 56. Channels 56 provide access to the approximated tissues when the arms are adjacent to each other. Staplers 58 ride within channels 56, and can be advanced distally to deploy fasteners 24 (here again illustrated as staples) while the roughened fold retainers 54 extend within the folded tissue surfaces. Roughened retainers 54 can abrade adjacent portions of the adjacent tissue surfaces defining the fold when pivotal probe 50 is withdrawn proximally, thereby promoting the formation of adhesions.

Referring now to 10A–10F, an alternative plication probe 60 forms fold 22 by grasping endopelvic fascia EF with jaws 62 of a forceps or forceps-like structure 64. Jaws 62 are then withdrawn proximally into a fixed channel 66. The endopelvic fascia forms fold 22 by sliding along slide surfaces 68 on either side of channel 66. Once forceps 64 have been withdrawn proximally by a distance which provides the desired fold length, the approximated regions of the endopelvic fascia can be affixed together.

As illustrated in FIG. 10E, fold 22 may be affixed at least in part using radiofrequency electrical current. Slide surfaces 68 include conductive electrode regions, so that application of an electrical potential between the slide surfaces directs the current 70 through fold 22. This radiofrequency energy may be used to shrink the tissues and/or promote adhesions between the proximated tissue surfaces upon healing. Fold 22 may further (or alternatively) be affixed using fasteners 22 deployed by stapler 58, as described above. In still further alternatives, a fastener may be advanced from one of slide surfaces 68 towards the other slide surface. Regardless, such fasteners will generally extends at least part way through each of first region 72 and second region 74 of endopelvic fascia EF defining fold 22. Once regions 72, 74 are affixed together, fold 22 can be released from probe 60, and will maintain the endopelvic fascia EF in the shortened configuration.

Figure 11:
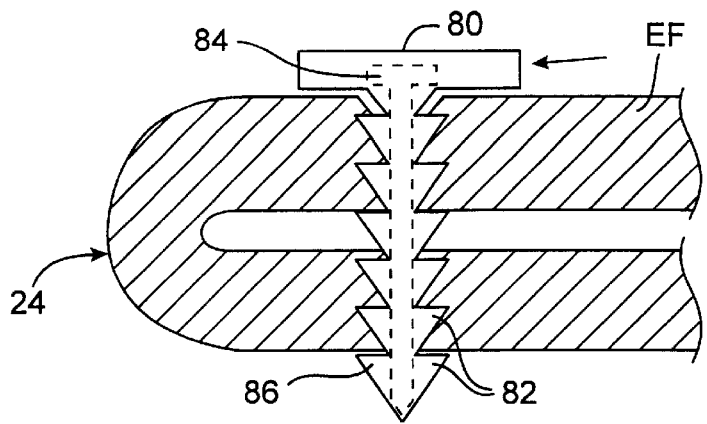
FIG. 11 is a cross-sectional view through a fold in the endopelvic fascia in which the fold is affixed using a reabsorbable barbed tack.

Referring now to FIG. 11, an alternative fastener for maintaining fold 24 in the endopelvic fascia EF comprises an absorbable tack 80 having one or more barbs 82. Optionally, tack 82 can be used as an electrode to affect monopolar or bipolar heating of the tissue so as to promote the formation of adhesions. Such a conductive tack may comprise magnesium or a magnesium aluminum alloy structure 84, and may optionally further include a reabsorbable suture material 86 such as those described in U.S. Pat. Nos. 5,576,418; 5,227,412; 4,994,074; and 4,776,329, the full disclosures of which are incorporated herein by reference.

Figure 12:
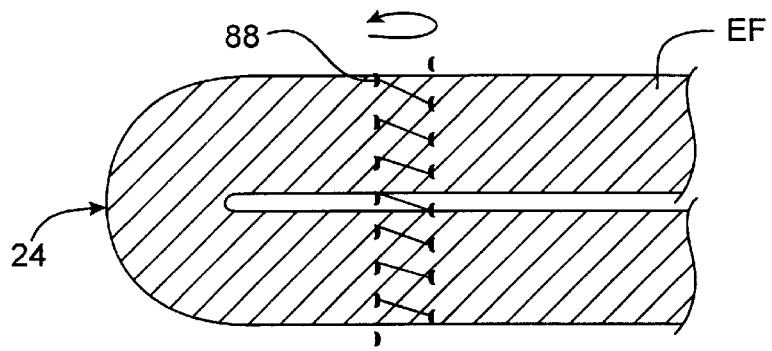
FIG. 12 is a cross-sectional view through a fold in the endopelvic fascia in which the fold is affixed using a helical coil.

A still further alternative of fastening structure is illustrated in FIG. 12. A helical coil 88 may be advanced into fold 24 of endopelvic fascia EF by rotating the coil into the tissue. The coil may be used as an electrode to promote the formation of adhesions, and/or may be reabsorbable. Alternatively, coil 88 (or any of the other fasteners described hereinabove) may comprise materials such as titanium or stainless steel, which are biocompatible but are not resorbed, thereby providing permanent fixation of the fold.

Figure 13:
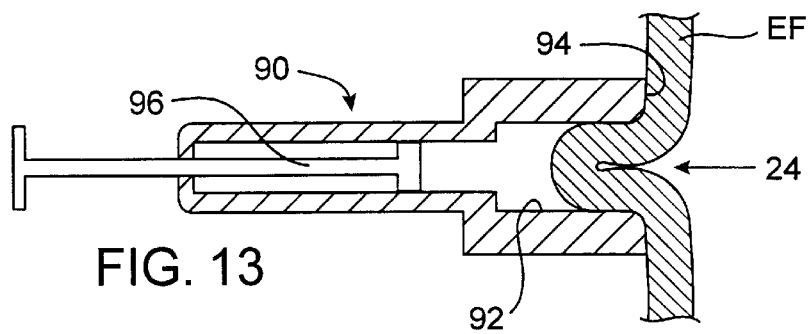
FIG. 13 is a cross-sectional view schematically illustrating the structure and use of a probe having a vacuum cavity to draw a fold of the endopelvic fascia therein.
Figure 14:
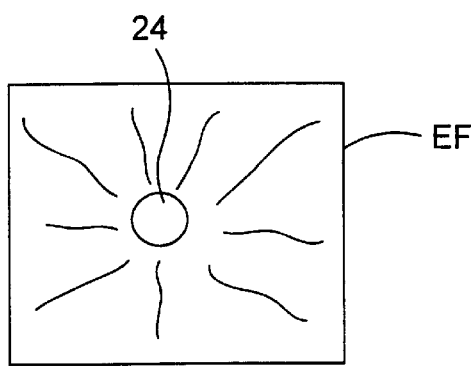
FIG. 14 illustrates a fold in the endopelvic fascia which is centered about a point, as might be formed by the plication tool of FIG. 13.

An alternative mechanism for drawing the fascia inward can be understood with reference to FIG. 13. A vacuum probe 90 includes a distal cavity 92 having a rim 94. Rim 94 engages a surface of endopelvic fascia EF, and a piston 96 draws a vacuum in cavity 92 so that endopelvic fascia is drawn inward into the cavity, thereby defining fold 24. As can be understood with reference to FIG. 14, fold 24 may here comprise a bunched region of fascia centered around a point. Alternatively, cavity 92 may be elongate so as to form an elongate fold as described hereinabove.

Once vacuum probe has approximated regions of the endopelvic fascia so as to define fold 24, the approximated tissue may be fixed together using staples, barbed tacks, radiofrequency energy, sutures, or the like. Once again, these affixing mechanisms may be deployed using structures incorporated into vacuum probe 90, although the scope of the present invention encompasses the use of separate tissue fixation deployment mechanisms.

A method for accessing a target region of the endopelvic fascia for plication is illustrated in FIGS. 15A–D. In general, endopelvic fascia EF can be viewed as left and right fascial portions separated at the patient's midline by urethra UR. Endopelvic fascia EF is supported by ligaments ATFP above a vaginal mucosa VM. It may be desirable to selectively decrease a length of endopelvic fascia EF along target regions 140 which extend in an anterior posterior direction along the left and right sides of the endopelvic fascia. This should provide enhanced support of urethra UR, the bladder neck, and the bladder with little risk of injuring the delicate urethral tissues.

Figure 15A:
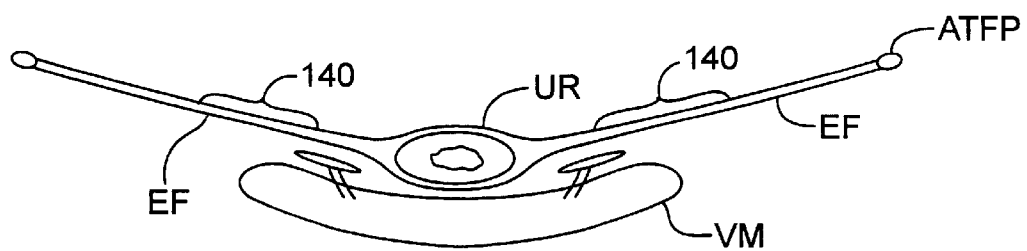
FIGS. 15A–D schematically illustrate a method for accessing left and right target regions of the endopelvic fascia.
Figure 15B:
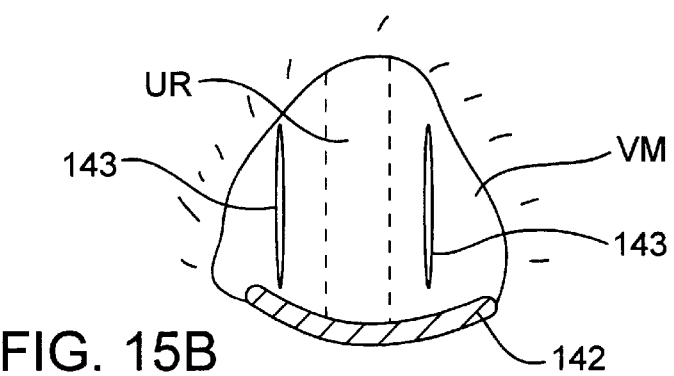
Figure 15C:
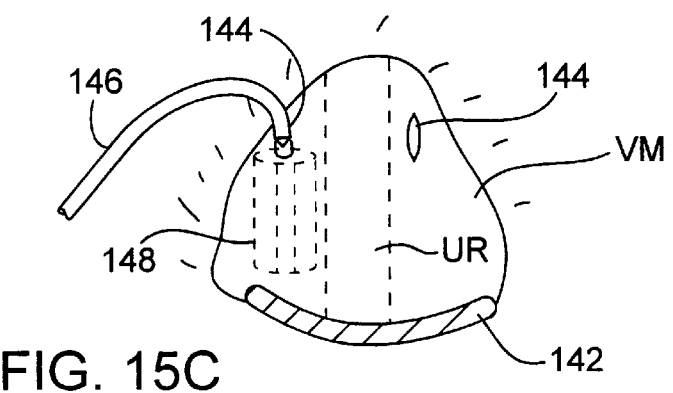
Figure 15D:
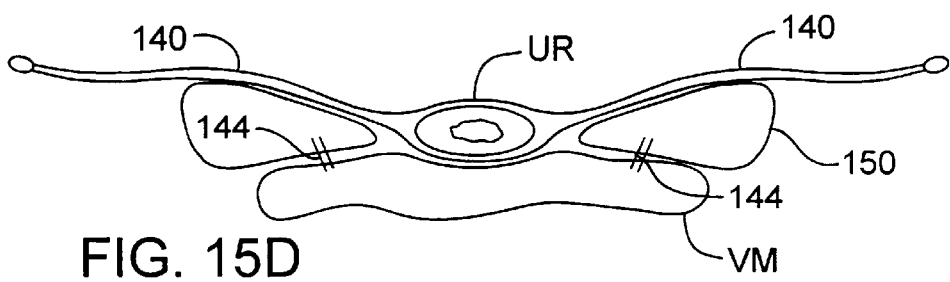

To access target regions 140 with minimal trauma to the patient, a weighted speculum 142 is inserted into the vagina to expose the vaginal mucosa VM. Optionally, elongated laterally offset incisions 143 might be made in the vaginal mucosa so that the vaginal mucosa could be manually dissected from the endopelvic fascia EF. However, to minimize trauma and speed healing, a small incision 144 may be made on either side of urethra UR allowing access for a minimally invasive blunt dissection device 146. Dissection device 146 includes a mechanical expansion element in the form of a balloon 148 at its distal end. Balloon 148 dissects the back side of the mucosa from the endopelvic fascia to create a minimally invasive treatment site 150 along each of the discrete target regions 140, as seen in FIG. 15D. Minimally invasive plication probes may then access the exposed target regions through incisions 144.

Figure 16:
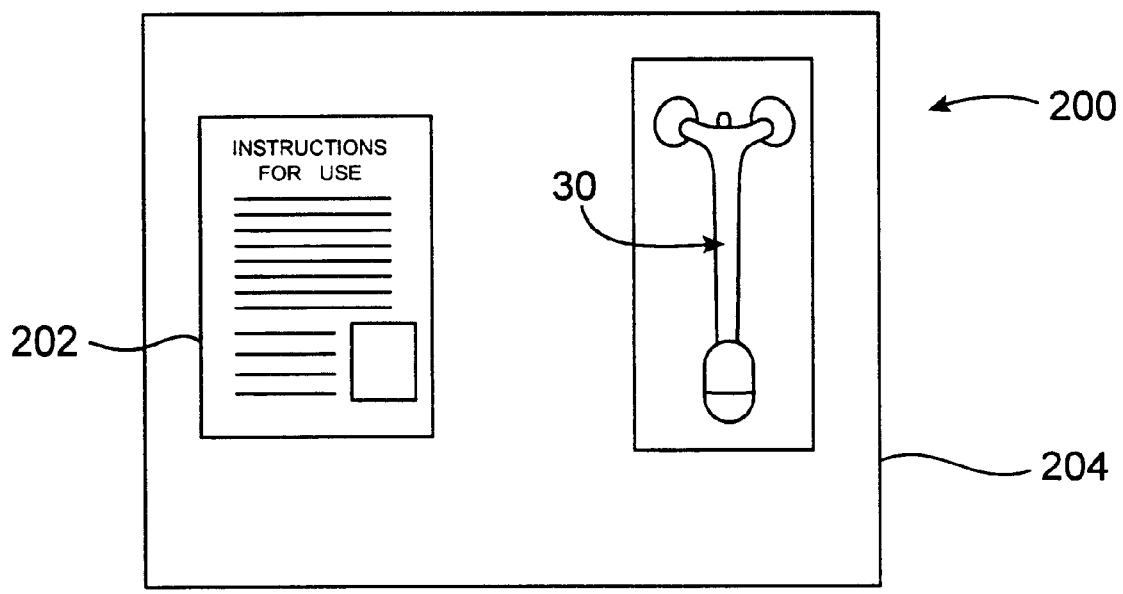
FIG. 16 illustrates an incontinence therapy kit including the probe of FIGS. 8.

Referring now to FIG. 16, a kit 200 includes probe 30 and instructions 202 for use of the probe to plicate tissues, the probe and instructions disposed in packaging 204. The instructions may set forth any of the methods for using probes described hereinabove for selectively decreasing an effective length of pelvic support tissues as a therapy for urinary incontinence, or may alternatively recite any of the other described methods. Alternative probe structures may replace the specific embodiment illustrated, and other system elements may also be included in kit 202, or may be packaged separately.

Instructions 202 will often comprise printed material, and may be found in whole or in-part on packaging 200. Alternatively, instructions 202 may be in the form of a recording disk or other computer-readable data, a video tape, a sound recording, or the like.

The present invention further encompasses methods for teaching the above-described methods by demonstrating the methods of the present invention on patients, animals, physical or computer models, and the like.

While the present invention has been described in some detail, by way of example and for clarity of understanding, a variety of modifications, adaptations, and changes will be obvious to those of skill in the art. For example, the fold retainer structures of probes of FIGS. 8 and 9 may deploy cyanoacrylate adhesive within the fold so as to affix the approximated tissue surfaces together, rather than (or in addition to) deploying fasteners or radiofrequency current. Alternatively, affixing needles and sutures may be incorporated into the probes or deployed manually to affix the folds, or simple ligation-like loops of suture may be prepositioned around rim 94 of vacuum probe 90 to affix the bunched up fascia in place and reduce the effective length of the endopelvic fascia. Hence, the scope of the present invention is limited solely by the appended claims.

What is claimed is:

1. An endopelvic fascia plication tool comprising:
   a probe having a proximal end and a distal end;
   means for grasping a region of the endopelvic fascia and for forming a fold in the endopelvic fascia that extends away from the plication tool, the grasping means disposed near the distal end; and
   an actuation mechanism coupled to the grasping means so that actuation of the mechanism draws the grasped region inward from an initial configuration having an initial area to a smaller configuration having a smaller area.

2. A plication tool as claimed in claim 1, further comprising means for affixing the inward drawn region in the smaller configuration, the affixing means disposed near the grasping means.

3. A placation tool as claimed in claim 2, wherein the affixing means comprises a member selected from the group consisting of an electrode, adhesive, suture, a staple, a helical coil, and a barbed tack.

4. A plication tool as claimed in claim 2, wherein the affixing means is reabsorbable, and further comprising means for promoting adhesion formation, the adhesion promoting means oriented for engaging a surface of the endopelvic fascia disposed within the fold of the endopelvic fascia formed as the grasped region is drawn inward from the initial configuration to the smaller configuration.

5. An endopelvic fascia plication system comprising:

a probe having a proximal end and a distal end;

a grasper adjacent the distal end for engaging a surface region of the endopelvic fascia tissue and for forming a fold in the endopelvic fascia that extends away from the probe; and a first actuation mechanism coupled to the grasper so that actuation of the first mechanism draws the engaged tissue inward from an initial configuration to a smaller area configuration.

6. A plication system as claimed in claim 5, further comprising a fastener disposable near the grasper and a second mechanism coupled to the fastener such that actuation of the second mechanism advances the fastener at least partially through the tissue so as to affix the tissue in the smaller configuration.

7. A plication system as claimed in claim 5, further comprising an electrode disposed near the grasper and an electrical conductor extending proximally from the advanced fastener to a current source for application of sufficient current to affix the tissue in the smaller configuration.

8. A plication system as claimed in claim 5, wherein the grasper comprises a pair of elements having tissue engaging surfaces configured to unslidingly engage the endopelvic fascia, wherein actuation of the first mechanism moves the tissue engaging surfaces inward.

9. A plication system as claimed in claim 8, further comprising a fold element extendable distally between the graspers to shape a fold of the tissue as the first mechanism removes the tissue engaging surfaces inward.

10. A plication system as claimed in claim 9, wherein at least one of the tissue engaging surfaces comprises a circumferentially oriented surfaces of a ripper wheel.

11. A plication system as claimed in claim 9, wherein at least one of the tissue engaging surfaces is disposed on an arm pivotally coupled to a shaft of the probe.

12. A plication system as claimed in claim 9, wherein the fold element is configured to injure tissue engaged thereby so as to promote formation of adhesions.

13. A plication system as claimed in claim 12, wherein the fold element has a roughened outer surface.

14. An endopelvic fascia plication system comprising:

a probe having a proximal end and a distal end;

a grasper comprising actuatable jaws adjacent the distal end for engaging a surface region of the endopelvic fascia tissue; and a first actuation mechanism coupled to the grasper so that actuation of the first mechanism draws the engaged tissue inward from an initial configuration to a smaller area configuration into a fixed channel between a pair of slide surfaces.

15. An endopelvic fascia plication system comprising:

a probe having a proximal end and a distal end;

a grasper comprising a cavity having a rim oriented for engaging the tissue surface while the probe is positioned perpendicularly to the tissue surface; and a first actuation mechanism coupled to the grasper and extending along the probe between the proximal and distal ends so that actuation of the first mechanism evacuates the cavity to draw the tissue therein.

* * * * *